United States Patent [19]

Hsu et al.

[11] Patent Number: 4,775,447
[45] Date of Patent: Oct. 4, 1988

[54] PROCESS FOR THE PRODUCTION OF 2,2-DIMETHOXYPROPANE

[75] Inventors: Chao-Yang Hsu, Media; Paul E. Ellis, Jr., Downingtown, both of Pa.

[73] Assignee: Sun Refining and Marketing Company, Philadelphia, Pa.

[21] Appl. No.: 621,814

[22] Filed: Jun. 18, 1984

[51] Int. Cl.$^4$ .............................................. B01D 3/36
[52] U.S. Cl. ..................................... 203/62; 203/81; 203/DIG. 23; 568/594
[58] Field of Search ............. 203/50, 62, 81, DIG. 23; 568/591, 592, 594

[56] References Cited

U.S. PATENT DOCUMENTS

| | | | |
|---|---|---|---|
| 1,850,836 | 3/1932 | Guinot | 568/594 |
| 2,827,495 | 3/1958 | Bond et al. | 568/594 |
| 2,837,575 | 6/1958 | Waters et al. | 568/594 |
| 4,136,124 | 1/1979 | Zinke-Allmang et al. | 568/591 |
| 4,153,516 | 5/1979 | Reed et al. | 203/63 |

FOREIGN PATENT DOCUMENTS

| | | | |
|---|---|---|---|
| 2929827 | 2/1981 | Fed. Rep. of Germany | 568/591 |
| 0230778 | 4/1969 | U.S.S.R. | 203/50 |

OTHER PUBLICATIONS

Lorrette, *Chem. Eng. Prog. Symp.*, Ser. 63, p. 148 (1967).

*Primary Examiner*—David L. Lacey
*Assistant Examiner*—V. Manoharan
*Attorney, Agent, or Firm*—J. Edward Hess; Donald R. Johnson

[57] ABSTRACT

The process for the acid-catalyzed reaction of acetone with methanol to form 2,2-dimethoxypropane may be significantly improved if a stoichiometric ratio of methanol/acetone is employed in the initial reaction.

Of particular advantage is the use of stoichiometric amounts of reactants in order to (1) avoid the expense of using an excess of either reactant, and (2) facilitate the removal of the 2,2-dimethoxypropane as an azeotrope with the methanol, thereby avoiding costly and complex product recovery methods.

8 Claims, No Drawings

PROCESS FOR THE PRODUCTION OF 2,2-DIMETHOXYPROPANE

BACKGROUND OF THE INVENTION

Discussion of the Prior Art

This invention relates to a process for the preparation of 2,2-dimethoxypropane. More particularly, it relates to an improved process for the acid-catalyzed reaction of acetone with methanol to form 2,2-dimethoxypropane, and thereafter recovering the product as an azeotrope with one of the reactants, thereby avoiding the costly extraction methods employed by the prior art.

2,2-Dimethoxypropane is a value intermediate for the production of insecticides and fungicides. It is also used as a dehydrating agent for the removal of water from water-sensitive organic reactions. 2,2-Dimethoxypropane is produced by the equilibrium-controlled reaction of acetone with methanol as follows:

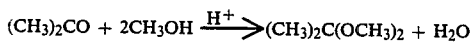

This reaction can be catalyzed by either soluble or insoluble strong acids. However, since the equilibrium is favored towards the starting materials, research has dealt with shifting the equilibrium to the 2,2-dimethoxypropane. For example, Lorrette [*Chem. Eng. Progr. Symp. Ser.* 63, P. 148 (1967)] has used low temperatures and high methanol/acetone feeds to increase the yield of 2,2-dimethoxypropane. His process is encumbered by the use of an uneconomical working temperature of $-27°$ C. He also uses a cost-intensive caustic extraction as part of his separation process.

Allmang and Scheimeir (GDR Pat. No. 2929827, 1981) use a ¼ molar ratio of methanol/acetone feed designed to produce an azeotropic mixture of acetone and methanol in addition to the 2,2-dimethoxypropane. However, their process suffers from the very low yield of 2,2-dimethoxypropane and subsequent high volumes of methanol/acetone which must be recycled, because in accordance with their recovery methods, a mole ratio of 4 parts of acetone must be used for each part of methanol in order to form said azeotrope.

Finally, the process described in U.S. Pat. No. 4,136,124 uses a dessicant, calcium sulfate, in large amounts to shift the equilibrium by removing the water produced in the reaction. Of course, this means an added cost due to replacement or regeneration of the spent calcium sulfate.

It is, therefore, an object of this invention to provide a process for the preparation and recovery of 2,2-dimethoxypropane which avoids the difficult and costly methods of the prior art.

SUMMARY OF THE INVENTION

In accordance with the present invention it has now been found that 2,2-dimethoxypropane may be produced from acetone and methanol in high yield and in a simplified manner at low cost and high energy savings in a process wherein stoichiometric ratios of acetone and methanol are reacted together in the presence of a strong acid-based ion-exchange resin, i.e., 2 parts methanol by volume to each part acetone, and thereafter the 2,2-dimethoxypropane is recovered as an azeotrope with the methanol in degrees of purity up to 98%.

As will be seen from the following description, the process of the present invention is highly advantageous compared with those of the prior art in that much less reactant is employed than that of the Allmang patent, thus saving not only materials but more importantly energy required to recover the large volumes of azeotropes. In addition, after the initial distillation to remove the acetone/methanol azeotrope, the remaining material, as described in detail below, contains a sufficient concentration of product that it may, if desired, be used as a dehydrating agent in various processes in that form without further purification. The prior art processes, by contrast, all require additional recovery steps before the dimethoxypropane is in a useful form.

DESCRIPTION OF THE PROCESS

In carrying out this process, a stoichiometric mixture of methanol and acetone is desirably passed over a bed of a strong acid based ion-exchange resin at 0°–25° C. at atmospheric pressure. The resulting equilibrium mixture of methanol, acetone, water and 2,2-dimethoxypropane is then subjected to distillation for recovery of the 2,2-dimethoxypropane. Desirably, a first azeotrope consisting of about a 4:1 molar ratio of acetone/methanol is removed overhead which contains essentially all of the acetone and part of the methanol, but essentially none of the product. This material can be recycled by conventional means to the reaction.

From the same distillation column, whether batch or continuous mode is used, a second azeotrope consisting of approximately a 3:1 molar ratio of methanol/2,2-dimethoxypropane is then removed which contains essentially all of the product. This mixture may then be used in that form as a dehydrating agent for oxidative carbomethoxylation of ethylene to methyl acrylate or to dimethyl succinate as described by Fenton et. al. [J. Org. Chem., 37, 2034 (1972)]. Alternatively, to this recovered material may then be added additional acetone in an amount of about 4 times the molar content of the remaining methanol in order to help separate the methanol from the 2,2-dimethoxypropane. Since acetone boils close to the methanol/acetone azeotrope, a slight excess of acetone is desirable. At this point, the methanol/acetone azeotrope is removed and the substantially pure 2,2-dimethoxypropane is recovered either at the bottom of the column or, for even greater purity, overhead.

A small amount of a weak base such as sodium bicarbonate or sodium methoxide can be added to the distillation flask to prevent the reverse reaction between product and water. The process can be run continuously by conventional techniques or batchwise as described in the example.

In this process, ratios of the reactants are generally in the range of 1:1 to 1:3 moles of acetone:methanol, but preferably a stoichiometric ratio of 1:2 should be employed. Higher molar ratios of methanol/acetone can be used in order to achieve higher yields of a product if recycle of the resultant higher amounts of excess methanol is not critical. Also, other solvents such as acetonitrile and ethyl acetate can be used to remove the methanol as an azeotrope in the second distillation column if desired.

In carrying out the initial reaction, the ion-exchange resin column can be operated at temperatures of from between 0°–25° C. with the lower temperatures giving a higher yield of 2,2-dimethoxypropane but requiring some refrigeration of the column.

The distillation temperatures for separation of the reactants and products will vary depending upon which azeotrope is being removed, at ranges which can readily be determined by those skilled in the art. Thus, for example, when the azeotrope consisting of essentially all the acetone and some methanol is first removed, this should desirably be carried out at a temperature of about 50° to 60° C., and preferably about 55° C. The azeotropic distillation of 2,2-dimethoxypropane and methanol is then carried out at about 58° to 65° C., preferably about 62° C. Thereafter, the 2,2-dimethoxypropane may be recovered as bottoms, or further purified by distillation at about 83° C., leaving behind any residual impurities.

Amongst the catalysts which may be employed, many strong acid based ion-exchange resins are acceptable, including Amberlyst XN 1010 and Amberlyst 15 (from the Rohm and Haas Co.) and Dowex 50 (from the Dow Co.) Each of these resins is of the general class of resins having the composition comprising a sulfonic acid functionalized polystyrene-divinylbenzene copolymer. The preferred resin is Amberlyst XN 1010. The catalyst, as described above, is generally utilized in a column, although bed-like arrangements can also be employed. After continued use, these catalysts may then be regenerated by known means, as for example by treating them with strong acids such as nitric, hydrochloric or sulfuric acid.

Advantages of using ion-exchange resins instead of the sharing acids of the prior art include simple separation of product avoidance of side reactions including no mesityloxide formation. Thus, the use of this type of catalyst has the unexpected benefit of a fast and clean reaction.

The invention will now be illustrated by, but is not intended to be limited to, the following examples.

EXAMPLE 1

This example will illustrate the production of 2,2-dimethoxypropane using the process of this invention.

A one-inch diameter column is filled with 9.45 g. of dry Amberlyst XN 1010 (preconditioned by an acid wash in the usual manner) giving a 2.5 cm. height in the column. The column is operated at room temperature with a feed containing 1620 ml. of methanol and 1468 ml. of acetone. The flow used is 20 ml/min. Once removed from the column, the effluent contains 1509 ml. of methanol, 1367 ml. of acetone, 168.6 ml. of 2,2-dimethoxypropane, and 24.7 ml. of water as analyzed by gas chromatography. To this mixture is added 1-2 g. of sodium bicarbonate. Using a 30 tray distillation column of one-inch diameter, 220 ml. of methanol/1332 ml. of acetone as an azeotrope is removed at 55°–56° C. At 62° C. an azeotrope containing 206 ml. methanol and 152 ml. of 2,2-dimethoxypropane is removed from the column. This material containing most of the product is added to a second 30 tray, one-inch diameter distillation column which has been charged with 1500 ml. of acetone. The methanol/acetone azeotrope is removed at 55°–58° C. leaving 146 ml. of 2,2-dimethoxypropane which is 98% pure and contains only a trace of acetone.

What we claim is:

1. In the process for the production of 2,2-dimethoxypropane by reacting methanol with acetone in the presence of an acidic catalyst, the improvement wherein the ratios of acetone to methanol are in the range of 1:1–1:3, and wherein the 2,2-dimethoxypropane is recovered by:
  (a) distilling off a first azeotrope comprising substantially all the acetone and part of the methanol, thereby leaving a residue containing the remaining methanol together with essentially all of the 2,2-dimethoxypropane; and
  (b) distilling said residue and recovering therefrom a second azeotrope comprising a minor amount of the remaining methanol and essentially all the 2,2-dimethoxypropane.

2. The method of claim 1 wherein the first azeotrope comprises a molar ratio of acetone:methanol of about 4:1.

3. The method of claim 1 wherein the first azeotrope is recycled to the reaction mixture.

4. The method of claim 1 wherein the second azeotrope comprises a molar ratio of methanol:2,2-dimethoxypropane of about 3:1.

5. The method of claim 1 wherein to the recovered second azeotrope is added sufficient acetone to permit formation of an azeotrope of said acetone with said methanol, and distilling off said azeotrope to leave substantially pure 2,2-dimethoxypropane.

6. The method of claim 5 wherein acetone is added in amounts sufficient to form a molar ratio with the remaining methanol of about 4:1.

7. The method according to claim 5 wherein the acetone and methanol azeotrope is recycled to the reaction mixture.

8. The method of claim 1 wherein the ratio of acetone:methanol in the production of said 2,2-dimethoxypropane is 1:2.

* * * * *